(12) United States Patent
Hallman, Jr. et al.

(10) Patent No.: US 6,182,951 B1
(45) Date of Patent: Feb. 6, 2001

(54) METHOD AND APPARATUS FOR PROVIDING A PRECISE AMOUNT OF GAS AT A PRECISE HUMIDITY

(75) Inventors: Russell L. Hallman, Jr.; James C. Truett, both of Knoxville, TN (US)

(73) Assignee: Lockheed Martin Energy Systems, Inc., Oak Ridge, TN (US)

(*) Notice: Under 35 U.S.C. 154(b), the term of this patent shall be extended for 0 days.

(21) Appl. No.: 09/150,920

(22) Filed: Sep. 10, 1998

(51) Int. Cl.[7] ...................................... B01F 3/04
(52) U.S. Cl. .................. 261/130; 261/43; 261/64.3; 261/107
(58) Field of Search ...................... 261/104, 107, 261/130, 42, 43, 64.3, DIG. 34; 239/44, 45

(56) References Cited

U.S. PATENT DOCUMENTS

| | | | |
|---|---|---|---|
| 4,036,915 | * 7/1977 | Lucero et al. | 261/104 |
| 4,474,051 | * 10/1984 | Fukuda et al. | 73/19.01 |
| 5,996,976 | * 12/1999 | Murphy et al. | 261/104 |

OTHER PUBLICATIONS

Kin–Tek, "Certified Cal–Gas Standards," Good Analysis Depends on Good Calibration, La Marque, Texas.
Kin–Tek, "Span Pac™ H$_2$O Standards Generator," Good Analysis Depends on Good Calibration, La Marque, Texas.
Sensors & Systems, Inc., "Air and Water Analyzers and Related Systems."
Mermoud et al., "Low–Level Moisture Generation," *Anal. Chem.*, vol. 63, No. 3, pp. 198–200 (Feb. 1, 1991).

* cited by examiner

Primary Examiner—Duane Smith
Assistant Examiner—Robert A. Hopkins
(74) Attorney, Agent, or Firm—Ackerman, Senterfitt, & Eidson, P.A.

(57) ABSTRACT

A fluid transfer system includes a permeable fluid carrier, a constant temperature source of a first fluid, and a constant pressure source of a second fluid. The fluid carrier has a length, an inlet end, and an outlet end. The constant pressure source connects to the inlet end and communicates the second fluid into the fluid carrier, and the constant temperature source surrounds a least of portion of the length. A mixture of the first fluid and the second fluid exits via the outlet end A method of making a mixture of two fluids is also disclosed.

19 Claims, 2 Drawing Sheets

METHOD AND APPARATUS FOR PROVIDING A PRECISE AMOUNT OF GAS AT A PRECISE HUMIDITY

STATEMENT REGARDING FEDERALLY SPONSORED RESEARCH OR DEVELOPMENT

This invention was made with government support under contract DE-AC05-96OR22464, awarded by the United States Department of Energy to Lockheed Martin Energy Systems Corporation, and the United States Government has certain rights in this invention.

FIELD OF THE INVENTION

This invention relates to a method and apparatus for introducing a precise amount of a first fluid into a second flowing fluid. This invention particularly relates to a new and improved method and apparatus for providing a precise amount of gas having a precisely controlled humidity.

Many applications in science and industry require an apparatus that creates a controlled amount of a first fluid to be introduced into a second fluid, such as a gas having a precise flow rate and a precisely controlled humidity. For instance, some material corrosion testing applications require such an apparatus to determine the reaction of a material over time upon exposure to a controlled liquid-gas mixture. Tests are typically performed using a higher liquid concentration of the liquid-gas mixture, in an effort to decrease the duration of the test. Data is then extrapolated to model the material's reaction over time. However, because the results are extrapolated, any error caused by an imprecisely controlled liquid-gas mixture will be magnified. Thus, the need for an apparatus that creates a controlled testing environment with a gas having a precise flow rate and a precisely controlled humidity is critical to ensure the accuracy of these types of tests.

A wide variety of conventional devices and methods used to produce a precise gas flow having a precisely controlled humidity are known in the art. Various systems introduce a liquid, such as water, into a gas stream using a calibrated leak. Generally, water is stored in a small vial having a very small orifice through which water vapor is metered. The humidity of the gas stream is modified by either adjusting the gas flow over the device or by adjusting the temperature of the vial. The accuracy of this apparatus is limited because changes in the gas stream flow rate or the temperature of the vial of water result in substantial changes in the humidity of the gas. Furthermore, this known apparatus requires controllers for varying gas flow and vial temperature.

Flow regulators and pressure regulators are distinct devices having different functions and characteristics. A pressure regulator differs from a flow regulator in that pressure regulators are actuated into opening or closing by sensing pressure of a fluid at its outlet, which regulation can be independent of the fluid flow. A flow regulator is actuated into opening or closing by sensing the flow rate of a fluid, which regulation can be independent of pressure.

Another conventional apparatus, known as a permeation cell, employs a permeable vial containing the liquid to be introduced into the gas stream. The liquid permeates through the vial and into the gas stream to produce the desired humidity. However, the aforementioned problems also affect this apparatus. In particular, vial temperature changes result in significant gas stream humidity changes. This apparatus also requires additional components for controlling gas flow.

Successive dilution is another known method for producing a precise gas flow with a precise humidity. With this method, dry gas is split into minor and major gas streams. After both gas streams are passed through separate flow controllers, the minor gas stream is passed through a liquid bubbler and reintroduced into the major gas stream. The reintroduction of the minor gas stream into the major gas stream produces the desired humidity. However, this method also has a number of inherent problems. First, the system requires that the major gas stream have a very large volumetric flow rate—on the order of liters per minute—to blend the gas streams to the required humidity. As a result, production of a product gas stream having a low flow rate cannot be practically accomplished. Also, costly detection equipment is required for measuring moisture vapor content. Further limitations of this method include the need for flow control valves in each gas stream, for controlling the process based on detection equipment data, and a proportional integral derivative controller for continuous adjustment of the flow control valves in order to maintain the desired humidity in the product gas stream.

SUMMARY OF THE INVENTION

It is an object of this invention to provide a fluid transfer system for introducing a first fluid into a second fluid flowing through a fluid carrier, wherein the system is designed for precisely controlling both the mixture rate of the fluids and the flow rate of the second fluid through the fluid carrier.

It is another object of this invention to provide a fluid transfer system capable of maintaining production of a precisely controlled fluid mixture under changing external conditions, such as fluctuations in ambient temperature and pressure.

It is another object of this invention to provide an instrument for independently verifying the calibration of dew point measurement devices.

It is another object of this invention to provide a fluid transfer apparatus that does not require costly components such as flow control valves, proportional integral derivative controllers, and humidity detection equipment.

In accordance with the present invention, these and other objects are accomplished by a fluid transfer system comprising a first fluid, a second fluid, a fluid carrier length having an inlet and an outlet, a constant temperature source for maintaining the first fluid at a constant temperature, and a constant pressure source connected to the fluid carrier inlet for introducing the second fluid into the fluid carrier at a constant pressure. The first fluid surrounds and permeates at least a portion of the fluid carrier length. A mixture of the first and second fluids is exhausted through the fluid carrier outlet.

In the preferred embodiment, a tubular fluid carrier is provided for directing the second fluid through the fluid carrier system. In this embodiment, the first fluid constant temperature source comprises a liquid bath, and the second fluid constant pressure source comprises a pressure regulator connected to the fluid carrier inlet.

A fluid transfer system in accordance with an alternate embodiment of the invention further comprises an inlet manifold, an outlet manifold, and at least one additional permeable fluid carrier length. In this embodiment, the constant pressure source is connected to the inlet manifold for regulating pressure which, in turn, regulates the flow of the second fluid into the inlet manifold. The first fluid surrounds and permeates at least a portion of each of the fluid carrier lengths, and a controlled mixture of the first and second fluids exits the fluid carrier lengths through the outlet manifold.

In yet a further embodiment of the invention, a fluid transfer system comprises a permeable fluid carrier tube having inlet and outlet ends, a water bath having a constant water temperature, and a gas source connected to the inlet end of the permeable fluid carrier tube via a pressure regulator. The gas source communicates a gas, through the pressure regulator, to the tube inlet. The pressure regulator fixes the pressure of the gas. The constant temperature bath surrounds and permeates at least a portion of the fluid carrier tube, allowing the water to mix with the flowing gas. A controlled mixture of dry gas and water vapor is expelled through the outlet end of the carrier tube. The flow rate of the gases through the tube is controlled, at least in part, by controlling the ratio of carrier tube inner diameter to carrier tube length.

A method of producing a mixture of a first and second fluids includes providing a first fluid at a constant temperature, communicating a second fluid at a constant pressure into an inlet end of a fluid carrier, submersing a length of the fluid carrier within the first fluid such that the first fluid permeates the fluid carrier to mix with the second fluid, and flowing the mixture toward an outlet end of the fluid carrier.

BRIEF DESCRIPTION OF THE DRAWINGS

There are shown in the drawings embodiments of the invention that are presently preferred, it being understood, however, that the invention is not limited to the precise arrangements and instrumentalities shown, wherein.

DETAILED DESCRIPTION OF THE PREFERRED EMBODIMENTS

Figure 1:
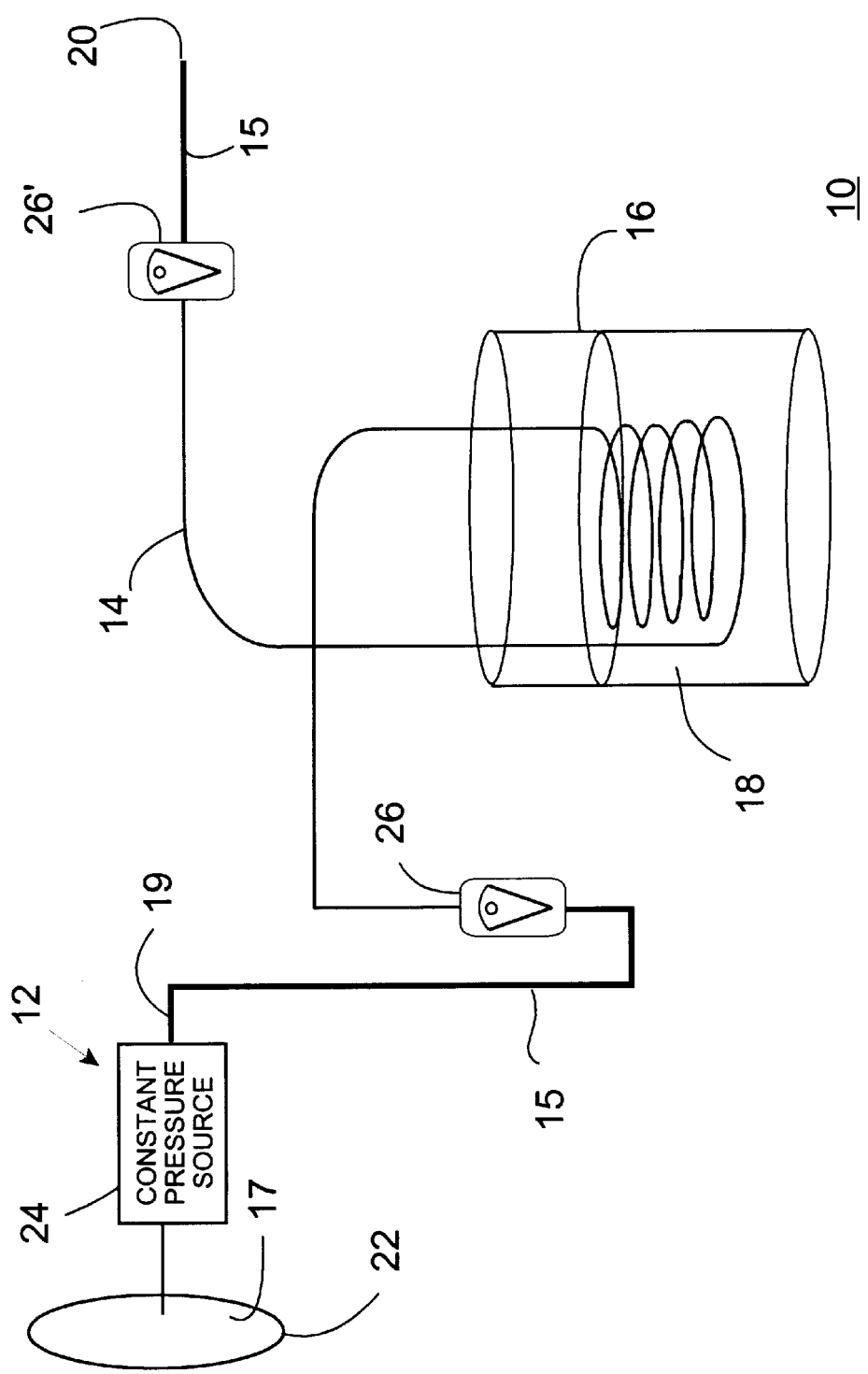
FIG. 1 is a schematic view of a fluid transfer system according to the invention.

FIG. 1 illustrates a fluid transfer system 10 according to the present invention. The fluid transfer system includes a fluid carrier for transporting a second fluid, contained in a second fluid source 22, from a fluid carrier inlet end 19 to a fluid carrier outlet end 20. In the best mode of the invention, the fluid carrier includes a permeable section 14 and impermeable sections 15, with the permeable and impermeable sections attached at air tight connection points 26 and 26'. In the preferred embodiment of the invention, the air tight connection points comprise flow measuring devices. A constant pressure source 12 is applied to second fluid 17. The constant pressure source 12 connects to the fluid carrier at inlet end 19 and provides a means for introducing second fluid 17 into the fluid carrier.

The fluid transfer system further comprises a first fluid 18 contained in a constant temperature source 16. The permeable section 14 of the fluid carrier is at least partially surrounded by first fluid 18. First fluid 18 permeates into fluid carrier 14 where it mixes as a vapor with second fluid 17. The fluid mixture is subsequently exhausted through outlet end 20. Although various fluid mixtures are possible, it is preferred that first fluid 18 is liquid water and second fluid 17 is a gas requiring humidification. It will occur to one skilled in the art that the fluid transfer system could include only permeable fluid carrier sections. In that case, the portion of the total length of the fluid carrier not surrounded by first fluid 18 should be minimized.

Constant pressure source 12 must be capable of communicating second fluid 17 into the fluid carrier at a uniform pressure. It will occur to one skilled in the art that a variety of constant pressure source arrangements are possible. In the preferred embodiment of the invention, constant pressure source 12 comprises a high pressure tank 22 containing second fluid 17, and connected to inlet end 19 of the fluid carrier by a pressure control device 24. Where source 22 is a fixed volume container, it is preferred that the container have sufficient volume such that the desired second fluid pressure is maintained during removal of second fluid 17 from the container.

Preferably, the pressure level provided by constant pressure source 12 can be varied via pressure control device 24. Numerous devices are available for controlling the pressure of constant pressure source 12. However, the preferred device is a pressure regulator. The fluid carrier has a fixed flow resistance which is dependent upon the ratio of fluid carrier diameter to fluid carrier length. The flow rate of second fluid 17 through the fluid carrier is proportional to the pressure exerted by pressure regulator 24. As a result, the flow rate of second fluid 17 through fluid carrier 14 can be controlled by manipulating pressure regulator 24.

As a general criteria, permeable fluid carrier 14 must be permeable to first fluid 18 and capable of transporting second fluid 17 across its entire length. Experiments were successfully performed using a capillary tube having a length of 6.096 meters, an inner diameter of 0.5875 mm, and an outer diameter of 0.762 mm. However, countless fluid carrier configurations are possible without departing from the scope of the invention. The configuration and dimensions of the fluid carrier directly influence the characteristics of the fluid transfer system. For instance, decreasing the fluid carrier inner diameter while holding the length constant, or increasing the fluid carrier length while holding the inner diameter constant, will produce a greater pressure drop across the length of the fluid carrier. In turn, the increased pressure drop will cause an increased resistance to flow and a corresponding decrease in the flow rate of second fluid 17 through the fluid carrier. Varying the flow rate of the second fluid provides one means of controlling the final mixture of first and second fluids, 18 and 17, with the rate of mixing inversely proportional to the flow rate of second fluid 17. Numerous other system variables can be manipulated to regulate the final fluid mixture, including, but not limited to: carrier tube permeability; carrier tube thickness; the length of carrier tube surrounded by the first fluid; first fluid temperature; and first fluid pressure.

It will occur to one skilled in the art that numerous fluid carrier materials could be employed. For example, possible materials include glass, Teflon and high-density polyethylene, to name just a few. The type of fluid carrier material used will directly impact the characteristics of the fluid transfer system. In particular, materials having high permeability to liquids, such as Teflon@, will allow a higher rate of fluid mixing than materials having a low rate of permeability, such as glass.

Generally, a specified length of permeable fluid carrier 14 is submersed in first fluid 18, such that first fluid 18 is able to permeate fluid carrier 14 and intermix with second fluid 17. The length of fluid carrier 14 which is submersed in first liquid 18 may be controlled to vary the characteristics of the fluid transfer system. Generally, increasing the length of fluid carrier 14 submersed in first fluid 18 will increase the quantity of first fluid permeating the fluid carrier and mixing with second fluid 17.

This invention is not limited as to the type of constant temperature source 16 that is used to keep first fluid 18 at a constant temperature. The source should be of sufficient size to accommodate a desired length of fluid carrier 14 to be surrounded by the first fluid, and the source should maintain the first fluid at a desired constant temperature. For instance, one preferred constant temperature source comprises a bath having a continuously circulated first fluid 18, wherein heating or refrigeration means are applied to maintain a desired constant temperature of first fluid 18 within approximately 0.1° C.

The temperature of constant temperature source 16 can be used to vary the permeation rate of first fluid 18 into second fluid 17, since changes in the temperature of the first fluid alter its permeation rate into fluid carrier 14. In particular, increasing the temperature of first fluid 18 will typically result in an increase in the permeation rate of first fluid 18 into fluid carrier 14, increasing the proportion of first fluid 18 in the final fluid mixture exhausted from the fluid carrier.

It is preferable to maintain first fluid 18 at a different temperature than the ambient temperature, since it is more difficult to maintain a constant first fluid temperature equal to the ambient temperature. Where an attempt is made to maintain equal first fluid and ambient temperatures, slight changes in ambient temperature, barometric pressure, or first fluid vaporization rate will cause a slight drift in the temperature of first fluid 18, actuating either heating or cooling of the first fluid. Because the temperature drift is minimal, refrigeration or heating tends to overcompensate for the drift, causing a greater temperature disparity.

Maintaining the first fluid temperature at a temperature other than ambient results in continuous application of either heating or refrigeration, thereby precluding the aforementioned undesirable effect of noncontinuous heating or cooling.

Figure 2:
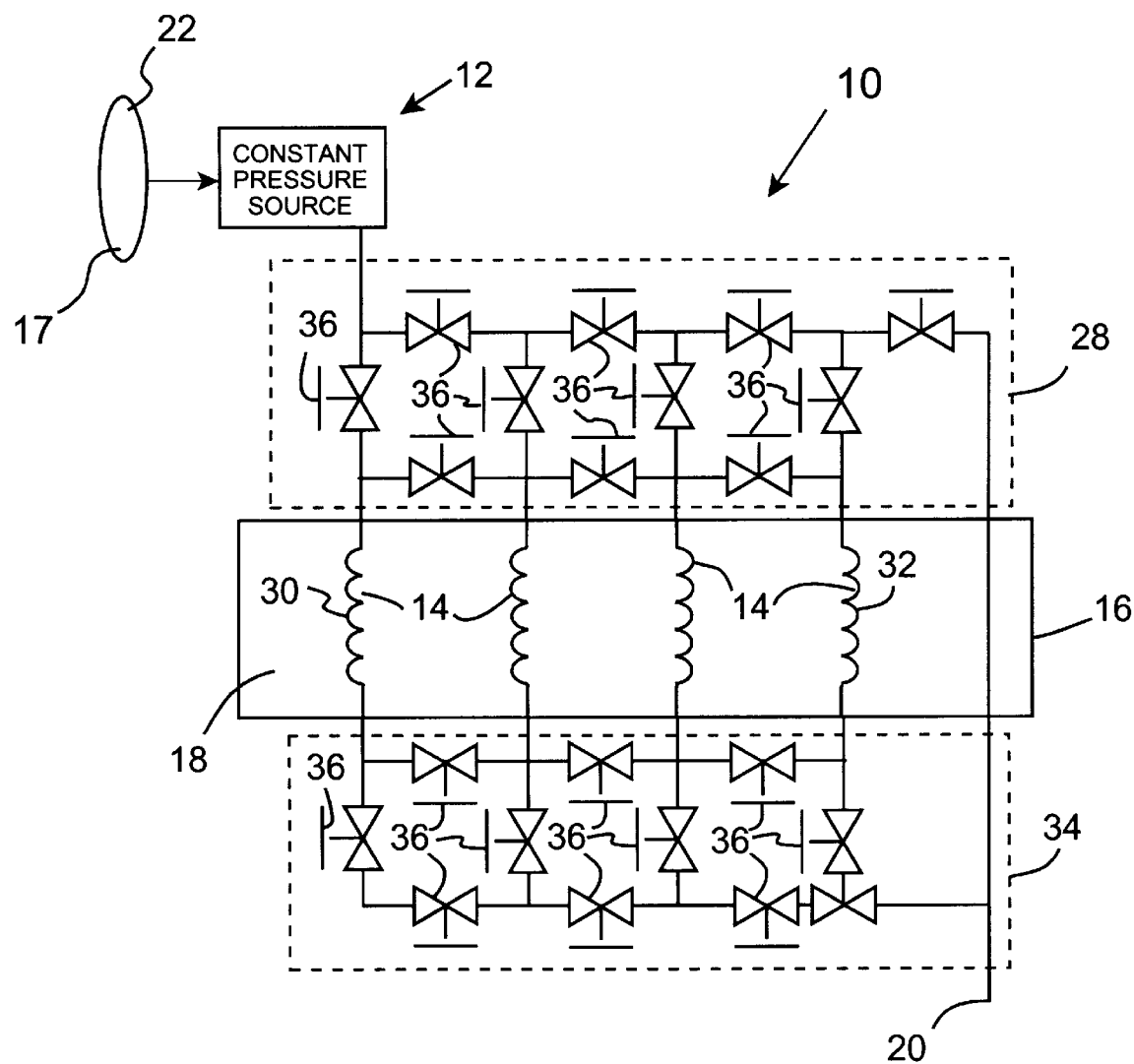
FIG. 2 is a schematic view of an additional embodiment of a fluid transfer system according to the invention.

Referring now to FIG. 2, in conjunction with FIG. 1, an alternate embodiment of the invention is shown. Fluid transfer system 10 includes: a constant pressure source 12 of a second fluid 17; an inlet manifold 28; a first length 30 of fluid carrier; at least one additional length 32 of fluid carrier; a constant temperature source 16 containing first fluid 18; and an outlet manifold 34. Constant pressure source 12 is fluidly connected to inlet manifold 28 for transporting second fluid 17 into the fluid carrier lengths 30, 32. Carrier lengths 30 and 32 are at least partially submersed in first fluid 18. First fluid 18 simultaneously permeates lengths 30 and 32, mixing with second fluid 17. Subsequently, the fluid mixture is transported to outlet manifold 34 and exhausted through outlet 20.

Preferably, manifolds 28 and 34 allow interconnection of fluid carrier lengths 30 and 32 in both series and parallel. The composition of the fluid mixture exiting the fluid transfer system can be varied by selectively connecting some fluid carrier lengths in parallel and others in series. Manifolds capable of producing series and/or parallel connections are well known in the art of fluid transfer systems. It is preferable that the manifolds 28, 34 include a number of interconnected valves 36 that can be opened or closed to produce either a series connection or a parallel connection between the carrier lengths 30, 32.

Each length comprises a permeable fluid carrier 14 that can either be immersed in a single constant temperature source or multiple constant temperature sources. Any quantity of additional lengths 32 is acceptable so long as each length 32 can fluidly communicate with the manifolds 28, 34 and is surrounded by a constant temperature source 16.

Connecting the carrier lengths 30, 32 in series effectively increases the total length of fluid carrier 14 immersed in first fluid 18. This increase in immersed carrier length results in a reduced flow rate of second fluid 17 through the fluid transfer system. Increasing the total length also increases the surface area through which the second fluid can intermix with the first fluid 18. Therefore, connecting a plurality of carrier lengths in series produces a reduced flow rate of second fluid 17 through the fluid transfer system and a higher pickup, or mixing rate, of the first fluid into the second fluid.

Connecting the carrier lengths 30, 32 in parallel has no effect on the total length of fluid carrier immersed in a first fluid 18 prior to exhaustion through outlet 20. Consequently, the permeation rate of the first fluid into the second fluid, or the mixing rate, will remain unchanged. However, the flow rate of the second fluid through the total system will increase proportionally with the quantity of carrier lengths 30, 32 in the system. For example, a total of two lengths will double the flow rate and a total of four lengths will quadruple the flow rate through the system. Thus, by varying the number of carrier lengths 30, 32 and their manner of connection (i.e., series or parallel), the output of the intermixed fluids at outlet end 20 can be varied.

The first step in operating the fluid transfer system of the instant invention involves setting system characteristics. Characteristics inherent to the physical construction of the system include fluid carrier length, material composition; and inner and outer diameter. Readily changeable characteristics of the fluid transfer system 10 include the pressure of the second fluid 17 entering the fluid carrier 14, the temperature of first fluid 18, and the composition of the first and second fluids. Other changeable characteristics are the number of individual carrier lengths 30, 32 employed and their relative arrangement in series and/or parallel.

In operation, a fluid transfer system 10 is provided and the first and second fluids are selected. The operator can vary the final fluid composition by varying the pressure of the second fluid entering the fluid carrier 14 (thereby changing the second fluid flow rate) and the temperature of the first fluid 18. Pre-calibrated pressure-temperature charts can be derived experimentally for particular fluid transfer systems. In particular, the charts provide the operator with relevant pressure and temperature settings to achieve desired flow rates and fluid mixtures. Typically, it is desirable to first determine the pressure level required to achieve a specified flow rate. Subsequently, a chart relating first fluid temperature to final fluid composition can be developed at the desired second fluid flow rate.

For instance, the following chart was derived experimentally for a given system. Initially, it was determined that a second fluid pressure of 15 pounds per square inch (psi) was required to produce a desired flow rate of 1.5 standard cubic feet per hour (scfh). Subsequently, the following table was derived based on the particular second fluid pressure setting (or flow rate):

| Temperature (° C.) | Content (PPM) |
| --- | --- |
| 35 | 19 |
| 40 | 21 |
| 45 | 30 |
| 50 | 42 |
| 55 | 60 |
| 60 | 82 |

Similar charts can be derived empirically for different fluid transfer systems according to the invention.

Producing the chart requires the use of a device capable of measuring the relative quantities of first and second fluids 17, 18 exiting the system. Specifically, the operator sets the pressure of the second fluid required to obtain the desired flow rate. Subsequently, the first fluid temperature is varied over a useful range. Upon stabilizing at each first fluid temperature set point, the relative composition of the exiting fluid is measured. A chart can be further developed by repeating the process for a desired range of flow rates.

Each chart is designed for use with a fluid transfer system 10 having particular system characteristics, such as fluid carrier materials and dimensions. Modifications to system characteristics which affect exhaust fluid composition warrant the production of additional charts. Although an operator can choose to vary either the temperature of the first fluid 18 or the pressure of the second fluid, it is preferred that the operator set the pressure of the second fluid at a described level to achieve a particular flow rate. Once the desired flow rate is achieved, the operator can vary the temperature of the first fluid 18 to obtain varying controlled compositions of the first and second fluids exiting the fluid transfer system 10.

The first step in constructing the system of the present invention entails determining the first and second fluids to be combined, since fluid selection affects the type of fluid carrier 14, constant temperature source 16, and constant pressure source 12 to be used. For instance, fluid carrier and constant temperature source material should be chosen to minimize reactivity with respective second and first fluids.

Once the characteristics of particular elements of the invention are determined, the construction of the fluid transfer system 10 requires that the permeable fluid carrier 14 is at least partially immersed in a volume of first fluid 18. As previously stated, the length of the fluid carrier 14 immersed in the first fluid is a characteristic affecting the mix rate of the first fluid into the second fluid.

The fluid carrier 14 must also be connected to a constant pressure source 12 of a second fluid. Any means of connecting the constant pressure source to the fluid carrier will suffice so long as the second fluid flows through the fluid carrier at a constant flow rate, when the second fluid is at a constant pressure.

The invention is capable of taking on alternative embodiments without departing from the spirit or essential attributes thereof. Accordingly, reference should be had to the following claims, rather than to the foregoing specification, as indicating the scope of the invention.

What is claimed is:

1. A fluid transfer system, comprising:
    a fluid carrier having a length, an inlet end, and an outlet end, said outlet end having an outlet pressure, said fluid carrier having a resistance to the flow of a given fluid;
    a constant pressure source of a second fluid attached directly to said inlet end for communicating said second fluid into said fluid carrier through said inlet end, whereby an amount of said second fluid flows through said fluid carrier in an amount equal to the pressure drop across said fluid carrier divided by said resistance; and
    a constant temperature source of a first fluid surrounding at least a portion of a permeable section of said fluid carrier length,
    whereby said first fluid permeates into said fluid carrier and intermixes with said amount of said second fluid, and a mixture of said first and second fluids exits said fluid carrier through said outlet end.

2. A fluid transfer system according to claim 1, wherein said fluid carrier is tubular.

3. A fluid transfer system according to claim 1, wherein said constant temperature source is a liquid bath.

4. A fluid transfer system according to claim 1, wherein said constant pressure source is a pressure tank connected by a pressure regulator to said inlet end.

5. A fluid transfer system according to claim 1, further comprising means for varying the temperature of said first fluid.

6. A fluid transfer system according to claim 1, further comprising means for varying the pressure of said second fluid.

7. A fluid transfer system, comprising:
    a constant pressure source of a second fluid connected to an inlet manifold, said constant pressure source attached directly to an inlet end of said inlet manifold for regulating the flow of a second fluid into the inlet manifold for communication of said second fluid through said system;
    a first permeable fluid carrier length and at least one additional permeable fluid carrier length, a first end of each said length fluidly connected to an output of said inlet manifold;
    a constant temperature source of a first fluid surrounding at least a portion of each said fluid carrier length; and
    an outlet manifold fluidly connected to a second end of each said fluid carrier length, whereby an amount of said second fluid flows through said system in an amount equal to the pressure drop across said system divided by the combined flow resistance of said inlet manifold, said fluid carrier lengths and said output manifold, and said first fluid permeates into each said length and intermixes with said amount of said second fluid, and a mixture of said first and second fluid exits said lengths through said outlet manifold.

8. A fluid transfer system according to claim 7, wherein said lengths are tubular.

9. A fluid transfer system according to claim 7, wherein said constant temperature source is a fluid bath.

10. A fluid transfer system according to claim 7, further comprising means for varying the temperature of said first fluid.

11. A fluid transfer system according to claim 7, further comprising means for varying the pressure of said second fluid.

12. A fluid transfer system comprising:
    a constant pressure source connected to an inlet manifold, said constant pressure source for regulating the flow of a second fluid into the inlet manifold;
    a first permeable fluid carrier length and at least one additional permeable fluid carrier length, each said length fluidly connected to said inlet manifold;
    a constant temperature source of a first fluid surrounding at least a portion of each said fluid carrier length; and
    an outlet manifold fluidly connected to each said fluid carrier length, wherein said inlet and outlet manifolds include valving means for connecting said lengths in series;
    whereby said first fluid permeates into each said length and intermixes with said second fluid, and a mixture of said first and second fluid exits said lengths through said outlet manifold.

13. A fluid transfer system comprising:
    a constant pressure source connected to an inlet manifold, said constant pressure source for regulating the flow of a second fluid into the inlet manifold;

a first permeable fluid carrier length and at least one additional permeable fluid carrier length, each said length fluidly connected to said inlet manifold;

a constant temperature source of a first fluid surrounding at least a portion of each said fluid carrier length: and an outlet manifold fluidly connected to each said fluid carrier length, wherein said inlet and outlet manifolds include valving means for connecting said lengths in a parallel;

whereby said first fluid permeates into each said length and intermixes with said second fluid, and a mixture of said first and second fluid exits said lengths through said outlet manifold.

14. A fluid transfer system comprising:

a constant pressure source connected to an inlet manifold, said constant pressure source for regulating the flow of a second fluid into the inlet manifold;

a first permeable fluid carrier length and at least one additional permeable fluid carrier length, each said length fluidly connected to said inlet manifold;

a constant temperature source of a first fluid surrounding at least a portion of each said fluid carrier length; and an outlet manifold fluidly connected to each said fluid carrier length, wherein said inlet and outlet manifolds include valving means for connecting said lengths in series and in parallel;

whereby said first fluid permeates into each said length and intermixes with said second fluid, and a mixture of said first and second fluid exits said lengths through said outlet manifold.

15. A fluid transfer system, comprising:

at least one water-permeable tube having an Inlet end and an outlet end, said outlet end having an outlet pressure, whereby said at least one tube has a resistance to the flow of a given gas;

a constant temperature liquid bath of water surrounding at least a portion of said permeable tube; and a constant pressure gas source directly connected to said inlet end for communicating a gas into said tube, whereby an amount of said gas flows through said system in an amount equal to the pressure drop across said system divided by the combined flow resistance of said at least one tube and said water permeates into said tube as a water vapor and intermixes with said gas and a mixture of said water vapor and said gas exits through said outlet end.

16. A fluid transfer system according to claim 15, wherein said gas source is connected by a pressure regulator to said inlet end.

17. A fluid transfer system according to claim 15, further comprising means for varying the pressure of said gas.

18. A fluid transfer system according to claim 15, further comprising means for varying the temperature of said water.

19. A method for producing a mixture of a first fluid and a second fluid, said first fluid having a substantially constant temperature, the method comprising the steps of:

communicating said second fluid at a constant pressure directly into an inlet end of a fluid carrier having a resistance to a flow of a given fluid, whereby an amount of said second fluid flows through said fluid carrier in an amount equal to the pressure drop across said fluid carrier divided by said resistance;

surrounding at least a section of said fluid carrier length with said first fluid;

permeating said first fluid through said fluid carrier and into said amount of second fluid, such that a mixture of said first and second fluids is produced; and exhausting said mixture through an outlet end of said fluid carrier.

* * * * *